United States Patent [19]

Mahar et al.

[11] Patent Number: 4,948,062
[45] Date of Patent: Aug. 14, 1990

[54] STERILE FILM DISPENSER FOR APPLANATING TONOMETER

[76] Inventors: Paul J. Mahar; Katie Mahar, both of 417 Glenwood Ct., Youngstown, Ohio 44512

[21] Appl. No.: 429,370

[22] Filed: Oct. 31, 1989

[51] Int. Cl.$^5$ .................. B65H 20/36; A61B 03/16
[52] U.S. Cl. .................. 242/67.3 R; 242/67.1 R; 128/645; 128/652
[58] Field of Search .......... 242/67.3 R, 67.1 R, 242/55.2; 128/645-652

[56] References Cited

U.S. PATENT DOCUMENTS

| | | |
|---|---|---|
| 1,004,630 | 10/1911 | Cotter . |
| 1,210,767 | 1/1917 | Cunha . |
| 2,536,592 | 1/1951 | Caesar et al. . |
| 2,566,582 | 9/1951 | Rotner . |
| 3,443,421 | 5/1969 | Posner et al. .................. 128/652 |
| 3,913,390 | 10/1975 | Piazza .................. 128/652 |
| 3,999,652 | 12/1976 | Overend .................. 242/67.3 R X |
| 4,333,637 | 6/1982 | Shelton . |
| 4,735,209 | 4/1988 | Foody .................. 128/652 |

Primary Examiner—Stuart S. Levy
Assistant Examiner—Steven M. duBois
Attorney, Agent, or Firm—Harpman & Harpman

[57] ABSTRACT

A sterile film device for use on medical instruments that supplies a continuous sterile film cover over the point of contact with the patient. The device utilizes a pair of distribution and take-up storage spools for dispensing guide sleeve and retrieval guides.

5 Claims, 2 Drawing Sheets

STERILE FILM DISPENSER FOR APPLANATING TONOMETER

BACKGROUND OF THE INVENTION

1. Technical Field:

This device relates to paper and film dispensing apparatus that are used to supply a clean disposable cover for medical equipment most notably examination tables and chair headrest.

2. Description of Prior Art:

Prior Art devices of this type have all been directed to medical and dental examination table and chairs usually with a dispensing roll of paper that is manually advanced over the surface and then removed after each use. Other applications have been directed towards safety covers for commodes and the like with no application for medical instruments such as eye examination devices.

Examples of prior art can be seen in U.S. Pat. Nos. 4,333,637, 2,566,582, 2,536,592, 1,004,630 and 1,210,767.

In U.S. Pat. No. 4,333,637 a chiropractic table is disclosed that has a paper retainer thereon that dispenses paper from a supply roll over two spaced headest with a tear-bar for removing used paper. The invention is directed to a spring urged release and tear bar. This allows the paper to be temporarily secured on the free end of the paper that can be selectively released for advancement of the paper and secured for manual removal.

In U.S. Pat. No. 2,566,582 a headrest cover for dental chairs is disclosed that comprises a pair of interconnected headrest configurations made of multiple layers of material with flexible backing and apertured sections.

U.S. Pat. No. 2,536,592 discloses a paper supply device for a headrest having a pair of dispensing and take-up reels positioned in side by side relationship in a hinge device secured to the chair. The clean paper is dispensed from the supply roll extending over the headrest and then returns around a guide rod under itself back to a take-up reel. Thus a continuous loop of supply and return papers established over the headrest.

A headrest for barber chairs is shown in U.S. Pat. No. 1,004,630 which includes a centrally mounted supply roll, and a pair of horizontally spaced guide and activation rollers. In use a crank handle on the activation roller is turned advancing a fresh portion of paper over and between said rollers.

Finally, in U.S. Pat. No. 1,210,767 a sanitary device for toilet seats is shown which comprises a supply roll of paper on one side of the seat and a pair of adjacent advancement rollers on the other side of the seat. A crank handle advances the paper over the seat. The paper has spaced apertures for registration with the opening defined in the seat.

SUMMARY OF THE INVENTION

A sterile film dispenser that provides a removable sterile film strip over the applanating head of a contact tonometer commonly used with a slit lamp to determine the intraocular pressure of the eye. The device and supply and retrieval spools with associated supply guide sleeve and retrieval guide secured to the instrument in neutral balanced positioning to maintain the instrument's required preliminary and graduated pressure settings.

DESCRIPTION OF THE PREFERRED EMBODIMENT

Figure 1:
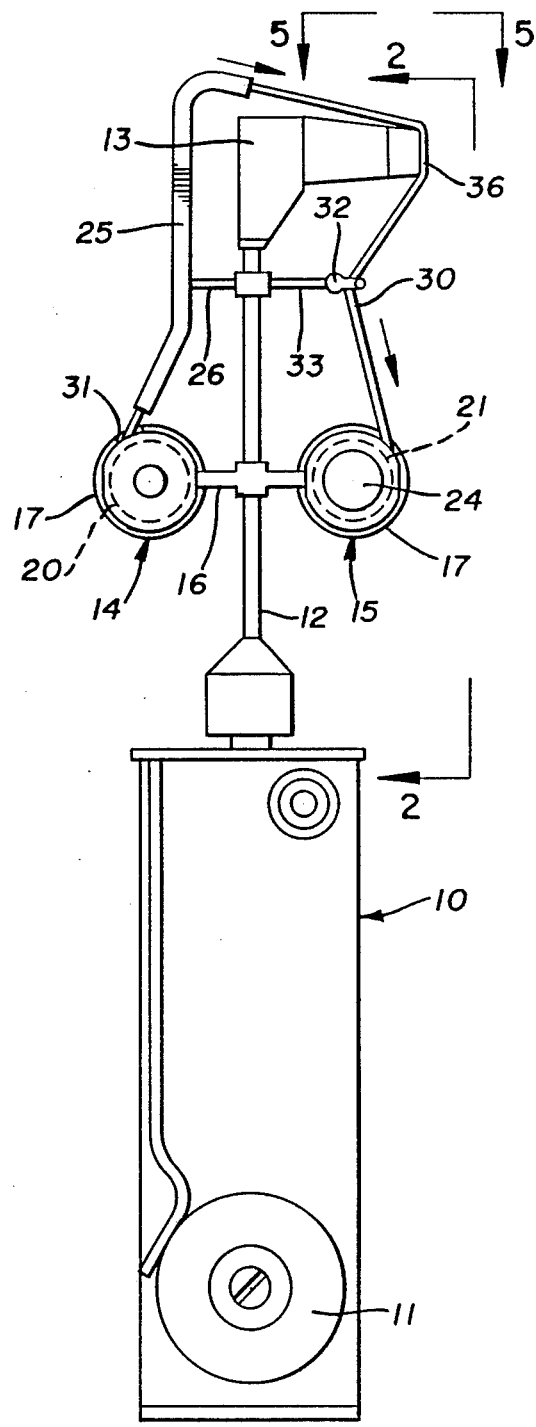
FIG. 1 is a side plan elevational view of a applanating tonometer with the sterile film dispenser mounted thereon.
Figure 2:
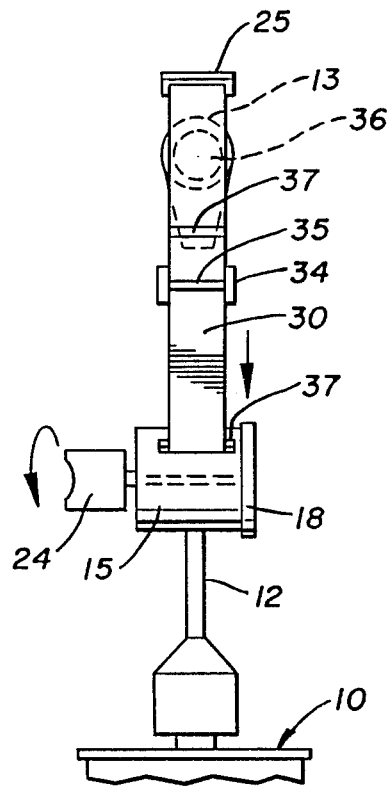
FIG. 2 is a partial front plan view on lines 5—5 of FIG. 1.

A sterile film dispensing device can be seen in FIGS. 1 and 2 of the drawings for use on an applanating tonometer comprises a base 10 having a control input dial 11 thereon. A measuring arm 12 extends vertically from said base 10 having an applanating head 13 positioned thereon. A further explanation of the applanating tonometer is deemed at this time unnecessary since the instrument is old and well known and understood by those skilled in the art and is used to measure the intraocular pressure of a human's eye. An example of such an instrument is the Goldmann applanating tonometer, Model T900, manufactured by Haag-Streit AG of Switzerland.

In use the applanating tonometer applanating head 13 is positioned against the patient's eye (not shown) and then slowly advanced against same thus calculating the intraocular pressure of the eye by the resistance occured against the measuring arm.

Figure 6:
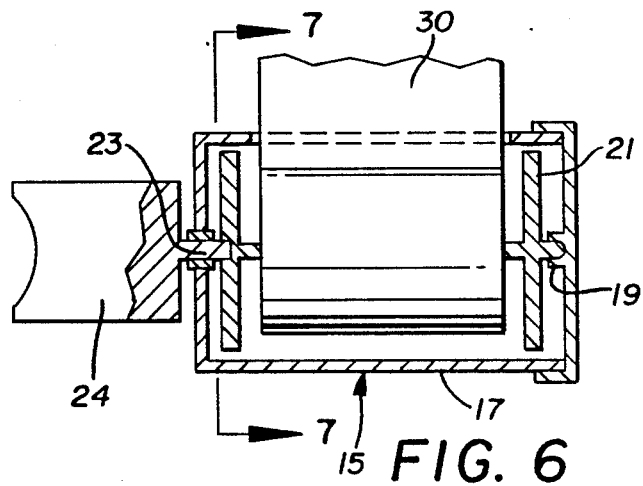
FIG. 6 is a cross-sectional view of a retrieval spool.
Figure 7:
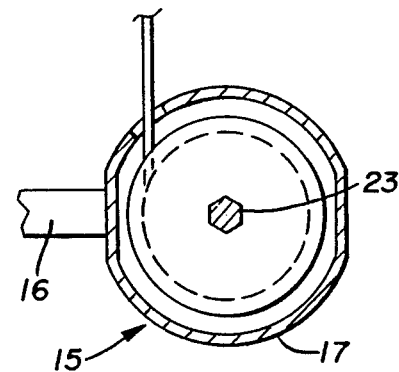
FIG. 7 is a sectional view on lines 7—7 of FIG. 6.

The sterile film dispenser device of the invention comprises a film dispensing spool 14 and a retrieval film spool 15. The spools 14 and 15 are secured to said measuring arm 12 via a support arm and clamp assembly 16. Each spool has a support case 17 with a removable end wall 18 which is journaled at 19, best seen in FIG. 6 of the drawings. Supply and take-up reels 20 and 21 are rotatably positioned in said respective spools 14 and 15 as seen in broken lines in FIG. 1 of the drawings. The take-up reel 21 as seen in FIGS. 6 and 7 of the drawings has a keyed journaled end 22 that accepts a registrable activation drive shaft 23 extending from an activation knob 24.

It will be evident from the above description that by manual rotation of the knob 24 the keyed reel 21 will rotate about its central axis within the support case 17.

Figure 3:
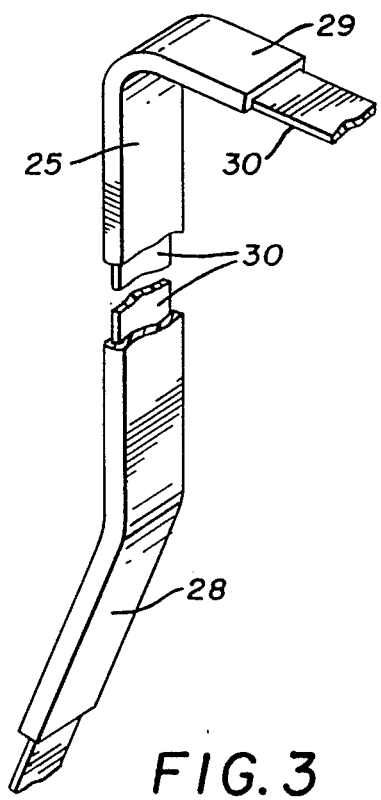
FIG. 3 is an enlarged perspective view of a guide sleeve positioned on the device.

Both of the reels 20 and 21 are restricted from free rotation by the nature of the friction fit within the journated end walls 18 and 19. A delivery sleeve 25 extends vertically in spaced relation from said spool 14 and is secured to the measuring rod 12 by a support clamp assembly 26. The delivery sleeve 25 can best be seen in FIG. 3 of the drawings comprising a transversely flattened sleeve having a main body member 27, an angular inclined feed portion 28 and a right angularly descending dispensing portion 29. The delivery sleeve 25 is rigid and is positioned so as to receive an end of a sterile band of flexible transparent material 30 which is stored in spiral rolled configuration around said reel 20 within said spool 14. The band of flexible transparent material 30 exits the spool 14 via an enlarged slot at 31. The delivery sleeve 25 extends from a point just above the spool 14 to a point extending above the upper most horizontal plane of the applanating head 13 as best seen in FIG. 1 of the drawings. A retrieval guide 32 extends from and is secured to said measuring rod 12 in oppositely disposed spaced relation to said dispensing sleeve 25 by an extension 33 of said support and clamp assembly 26.

The retrieval guide 32 comprises a bifurcated support arm 34 having a guide bar 35 extending between its respective free ends.

Figure 4:
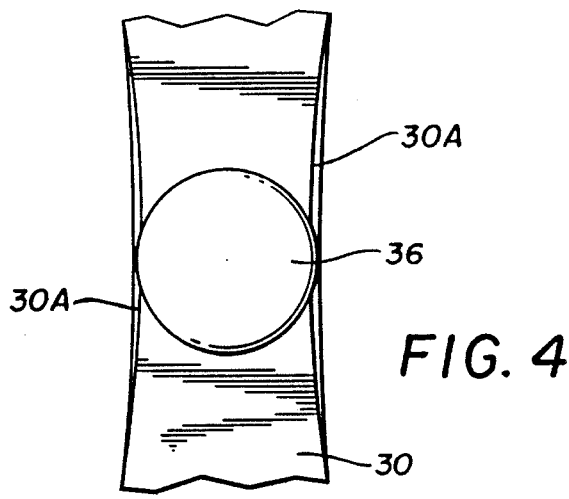
FIG. 4 is an enlarged view of a portion of the sterile film over the instrument.

In operation the band of flexible transparent material 30 extends from the spool 14 as hereinbefore described passes through the dispensing sleeve 25 and exits same above said applanating head 13. The band of flexible transparent material 30 extends over and engages said applanating head 13 at a patient engagement surface 36 characterized by the circular "footprint" seen in FIG. 4 of the drawings. The band of flexible transparent material 30 extends through said retrieval guide 32 and enters the spool 15 via a secondary elongated slot 37 and said enclosed reel 21 as best seen in FIGS. 2,6 and 7 of the drawings.

Figure 5:
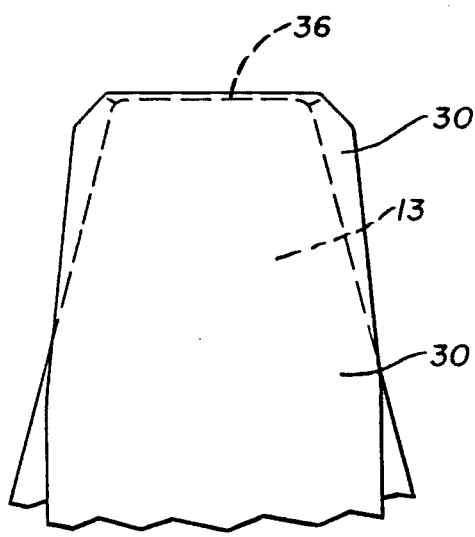
FIG. 5 is an enlarged view on lines 5—5 of FIG. 1.

Referring now to FIG. 5 of the drawings a portion of the applanating head 13 can be seen including the patient engagement surface 36 with the band of flexible transparent material 30 positioned thereover. It will be evident that since the transverse dimension of the material 30 is greater than the overall "footprint" of patient engagement surface 36 the band of transparent material 30 will fold over the respective engagement edges 30A of the patient engagement surface 36 forming a flexible channel configuration over the patient engagement portion 36 of the applanating head 13 maintaining the band of transparent material 30 alignment thereon.

The retrieval guide 32 which is positioned inwardly of the patient engagement portion 36 maintains the band of tranparent material in relative positon over the microscope head 13 and defines a film path alignment to the retrieval spool 15 as seen in FIG. 2 of the drawing.

By rotation of the knob 24, the retrieval spool 15 will steadily advance the band of transparent material 30 providing a fresh sterile surface for engagement with the patient's eye to be measured. Indicator bars 37 may be superimposed on the transparent material 30 in spaced transversed pairs to visually guide the user when advancing the material 30 so that a new sterile section defined between the indicator bars 37 will always be properly positioned over the patient enegagement surface 36 of the applanating head 13 as hereinbefore disclosed.

Thus, it will be seen that a new and useful sterile film dispensing device for medical instruments has been illustrated and described and that it will be apparent to those skilled in the art that various changes and modifications may be made therein without departing from the spirit of the invention, therefore I claim:

1. A sterile film band dispensing device for use on a applanating tonometer having a microscope head having a predetermined engagement area comprises, a pair of oppositely disposed dispensing and retrieval spools, means for securing said spools to said applanating tonometer, a sterile film band of transparent material removably positioned within said dispensing spool, a guide sleeve secured in spaced relation to said dispensing spool for receiving said sterile film material within, means for defining a guide path for engagement film of said sterile film band with said microscope head, means for advancing said sterile film band from said dispensing spool through said guide sleeve and over said microscope head.

2. The sterile film band dispensing apparatus of claim 1 wherein said means for securing said spools to said applanating tonometer comprises a support and clamping assembly extending from said applanating tonometer to said spools and centered therebetween.

3. The sterile film band dispensing apparatus of claim 1 wherein said sterile film band has an area which is greater than the predetermined engagement area of the microscope head.

4. The sterile film dispensing device of claim 1 wherein said means for advancing said sterile film band comprises a rotatable activation knob on said retrieval dispenser.

5. The sterile film dispensing device of claim 1 wherein said guide sleeve extends above a horizontal plane defined by an uppermost surface of said microscope head on said applanating tonometer.

* * * * *